(12) United States Patent
Schoeneck et al.

(10) Patent No.: US 9,415,386 B2
(45) Date of Patent: Aug. 16, 2016

(54) WASH THROUGH PIPETTOR

(71) Applicant: Douglas Scientific, LLC, Alexandria, MN (US)

(72) Inventors: Richard J. Schoeneck, Alexandria, MN (US); Paul H. Wagner, Alexandria, MN (US)

(*) Notice: Subject to any disclaimer, the term of this patent is extended or adjusted under 35 U.S.C. 154(b) by 0 days.

(21) Appl. No.: 14/776,505

(22) PCT Filed: Mar. 14, 2014

(86) PCT No.: PCT/US2014/028505
§ 371 (c)(1),
(2) Date: Sep. 14, 2015

(87) PCT Pub. No.: WO2014/144201
PCT Pub. Date: Sep. 18, 2014

(65) Prior Publication Data
US 2016/0016161 A1    Jan. 21, 2016

Related U.S. Application Data

(60) Provisional application No. 61/792,453, filed on Mar. 15, 2013.

(51) Int. Cl.
*B01L 3/02* (2006.01)
*G01N 35/10* (2006.01)

(52) U.S. Cl.
CPC ............. *B01L 3/0234* (2013.01); *B01L 3/0217* (2013.01); *B01L 2200/0689* (2013.01); *B01L 2200/141* (2013.01); *B01L 2300/0829* (2013.01); *B01L 2300/0861* (2013.01); *G01N 35/1004* (2013.01); *G01N 35/1065* (2013.01)

(58) Field of Classification Search
CPC ....... B01L 3/0234; B01L 3/0275; B01L 3/02; B01L 3/0206; B01L 3/217; B01L 3/0231; B01L 2300/0861; B01L 2200/0689; G01N 35/1004; G01N 35/1065
See application file for complete search history.

(56) References Cited

U.S. PATENT DOCUMENTS

| | | |
|---|---|---|
| 3,076,659 A | 2/1963 | Kremer, Jr. |
| 3,190,661 A | 6/1965 | Wahl et al. |
| 3,568,735 A | 3/1971 | Lancaster |
| 3,712,794 A | 1/1973 | Farr |
| 3,935,734 A | 2/1976 | Keegan |

(Continued)

OTHER PUBLICATIONS

International Search Report and Written Opinion dated Dec. 8, 2014 for corresponding PCT Applicatioin No. PCT/US2014/028505.

*Primary Examiner* — Brian R Gordon
(74) *Attorney, Agent, or Firm* — Kinney & Lange, P.A.

(57) ABSTRACT

A pipettor includes a wash chamber between an upper plate, a lower plate, an upper seal, and a lower seal. The upper and lower seal retain each other and are located between the upper and lower plates. The pipettor includes a gasket located below the lower plate, a pipette tip retained by the gasket, and a piston with a tapered tip that passes through the plates, seals, and gasket into the pipette tip. The upper and lower seal isolate the piston from the wash chamber. The pipettor includes a channel defined by the piston, extending into the pipette tip, and an actuator that advances and retracts the piston. When the actuator retracts the piston such that the piston loses sealing contact with the lower seal and the wash chamber is supplied with wash fluid and pressurized, wash fluid passes through the groove in the upper seal and into the channel.

7 Claims, 5 Drawing Sheets

(56) References Cited

U.S. PATENT DOCUMENTS

| | | | |
|---|---|---|---|
| 4,046,291 A * | 9/1977 | Goda | B01L 3/0231 222/309 |
| 4,304,138 A | 12/1981 | Tervamaki | |
| 4,493,896 A | 1/1985 | La Motte, III et al. | |
| 4,496,657 A | 1/1985 | Coppersmith et al. | |
| 5,985,651 A * | 11/1999 | Hunicke-Smith | B01L 3/0217 165/177 |
| 6,143,252 A | 11/2000 | Haxo, Jr. et al. | |
| 6,374,683 B1 * | 4/2002 | Hunicke-Smith | B01L 3/5085 73/863.32 |
| 6,706,538 B1 | 3/2004 | Karg et al. | |
| 6,824,024 B2 | 11/2004 | Ingenhoven et al. | |
| 6,926,867 B1 * | 8/2005 | Liu | B01L 3/0217 422/501 |
| 7,185,551 B2 | 3/2007 | Schwartz | |
| 7,727,476 B2 | 6/2010 | Ingenhoven et al. | |
| 7,919,047 B2 | 4/2011 | Sinclair et al. | |
| 2004/0208793 A1 * | 10/2004 | Jarvimaki | B01L 3/0217 422/500 |
| 2004/0231438 A1 * | 11/2004 | Schwartz | B01L 3/0217 73/864.17 |
| 2005/0244303 A1 | 11/2005 | Ingenhoven et al. | |
| 2006/0008370 A1 * | 1/2006 | Massaro | B01L 3/0217 417/539 |
| 2007/0207062 A1 * | 9/2007 | Sinclair | B01L 3/0217 422/400 |
| 2009/0277285 A1 * | 11/2009 | Panzer | B01L 3/0217 73/864.13 |
| 2011/0027149 A1 * | 2/2011 | Uldry | B01L 3/0217 422/501 |
| 2013/0209328 A1 * | 8/2013 | Dresse | B01L 3/50273 422/505 |

* cited by examiner

US 9,415,386 B2

WASH THROUGH PIPETTOR

CROSS-REFERENCE TO RELATED APPLICATION(S)

This application claims priority from U.S. Provisional Application No. 61/792,453, filed Mar. 15, 2013 for "WASH THROUGH PIPETTOR" by Richard J. Shoeneck et al.

BACKGROUND

The present invention relates to pipettors for high throughput screening, and specifically to the use of a wash through pipettor for dispensing and aspirating.

Laboratories use pipettors to transfer liquids from one container to another. Automated pipettors for high throughput screening typically transfer liquid from one array of containers to another array of containers. The container arrays are most commonly 96 well or 384 well microtiter plates. The 96 array format uses 8 rows by 12 columns using 9 mm grid spacing. The 384 format uses twice the density with 16 rows by 24 columns using 4.5 mm grid spacing. When these pipettors are used, the tips need to be discarded or washed when changing liquids. The current method of washing the pipette tips is to aspirate wash fluid, and then dispense it into a waste container. The wash cycle is repeated many times to dilute the residue on the inside of the tips to an acceptable level.

Another concern with pipettors is dispense volume accuracy, especially at volumes less than 1 uL. When dispensing small volumes, the wetting and break-off behavior of the very small droplet at the tip is influenced by many factors. If the liquid prefers to wet to the target container (either dry or containing liquid already), then the liquid column in the pipette tip will experience a downward force as the liquid wets out into the target well. The amount of liquid dispensed is variable depending upon the wetting action as compared to the forces that will keep the rest of the liquid in the tip. Conversely, if the liquid is repelled from the target, then it may be pushed back up into the tip. The forces between the tips and containers are often random and variable. Current pipettors all have a sizeable volume of air above the liquid that acts as a coupling member between the piston and the liquid. The compressibility of the air and the vapor pressure therein create a weak coupling between the piston position and the fluid position.

SUMMARY

A pipettor includes an upper plate, a lower plate, and a wash chamber defined by a space between the upper plate and the lower plate. The pipettor further includes an upper seal with a groove and a lower seal, the upper seal located below the upper plate and retained by the lower seal, and the lower seal located above the lower plate and retained by the upper seal. The pipettor further includes a gasket located below the lower plate, a pipette tip retained by the gasket, and a piston with a tapered tip that passes through the upper plate, the upper seal, the lower seal, the lower plate, and the gasket into the pipette tip. The upper seal and the lower seal isolate the piston from the wash chamber. A channel is defined by the piston and extends into the pipette tip. The pipettor further includes an actuator for advancing and retracting the piston. When the actuator retracts the piston such that the piston loses sealing contact with the lower seal and the wash chamber is supplied with a wash fluid and pressurized, the wash fluid passes through the groove in the upper seal and into the channel defined by the piston.

A method of operating a pipettor includes retracting a piston with a tapered tip such that the piston passes through a lower plate and a lower seal and loses sealing contact with the lower seal, the lower seal retaining an upper seal with a groove and the upper seal retaining the lower seal. The method further includes supplying a wash chamber surrounding the lower seal and the upper seal with wash fluid and pressurizing the wash chamber such that the wash fluid passes through the groove of the upper seal into a channel defined by the piston, the channel passing through a lower plate below the lower seal, through a gasket below the lower plate, and into a pipette tip retained by the gasket. The method further includes advancing the piston such that the wash fluid flows through the channel, filling the pipette tip and such that the piston seals off the channel from the wash chamber.

DETAILED DESCRIPTION

Figure 1:
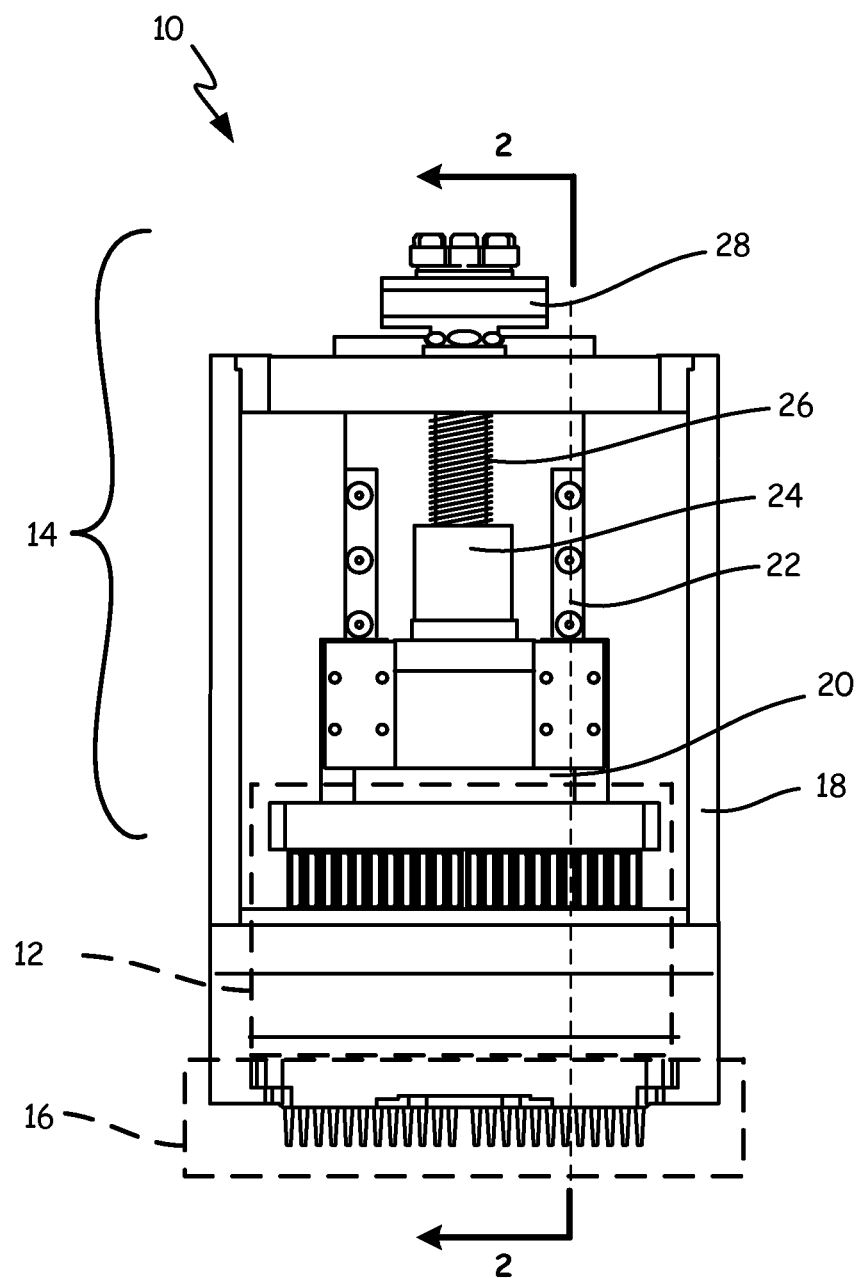
FIG. 1 is a front view of the wash through pipettor of the present invention.
Figure 2:
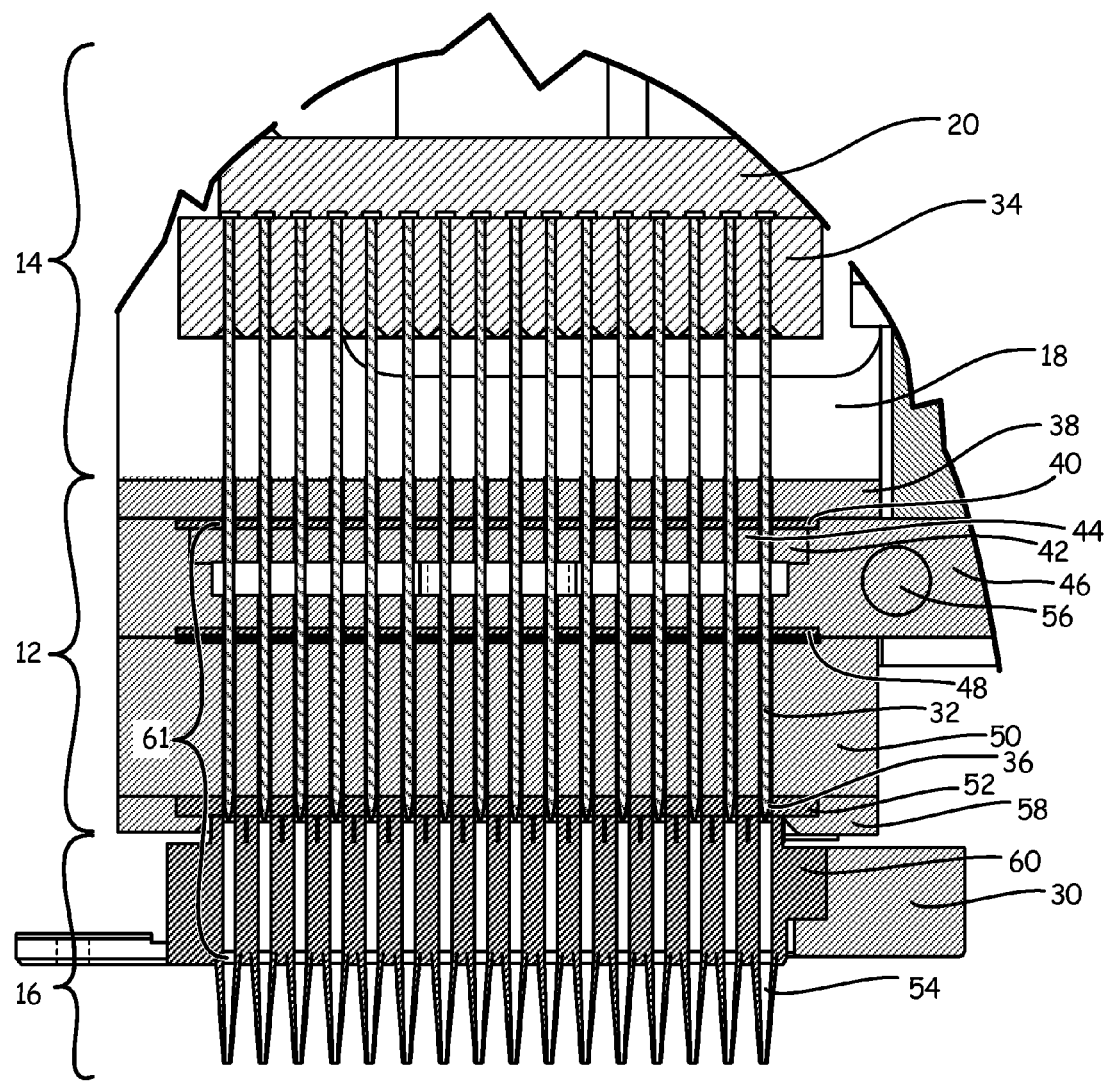
FIG. 2 is a cross-sectional view of the wash through pipettor of the present invention along line 2-2 in FIG. 1.

FIG. 1 is a front view of wash through pipettor 10. FIG. 2 is a cross-sectional view of wash through pipettor 10 along line 2-2 in FIG. 1. As shown in FIG. 1 and FIG. 2, wash through pipettor 10 includes piston assembly 12, actuator assembly 14, and tip tray 16. Actuator assembly 14 includes actuator frame 18, actuator plate 20, linear bearings 22, ball screw nut 24, ball screw 26, actuator motor 28, and tip tray clamp 30. Piston assembly 12 includes an array of pistons 32 with tapered tips 36, piston plate 34, top seal plate 38, upper seal 40, wash plate upper seal retainer 42, wash chamber 44, wash plate 46, lower seal 48, cylinder block 50, thru tip gasket 52, supply port 56, and tip gasket retainer 58. Tip tray 16 includes pipette tips 54 and tip holder 60.

Pistons 32 are connected to piston plate 34. Pistons 32 with tapered tips 36 pass through top seal plate 38, upper seal 40, wash plate upper seal retainer 42, wash chamber 44, wash plate 46, lower seal 48, cylinder block 50, and thru tip gasket 52. Pistons 32 define fluid flow channels 61. The volume capacity of each fluid flow channel 61 is determined by the cross section area of each piston 32 multiplied by the maximum stroke length. The maximum stroke length is the sum of the thickness of cylinder block 50 and the length that pistons 32 are allowed to advance down into the interior of pipette tips 54.

Wash plate 46 includes wash chamber 44 supplied with wash fluid via supply port 56. Upper seal 40 is retained between top seal plate 38 and wash plate upper seal retainer 42. Lower seal 48 is retained between wash plate 46 and cylinder block 50. Upper seal 40 and lower seal 48 are designed to seal around pistons 32. Thru tip gasket 52 is designed not to seal around pistons 32. Thru tip gasket 52 is designed to seal against the top rim of pipette tips 54. Thru tip gasket 52 is retained by tip gasket retainer 58. Tip tray 16 is loaded into tip tray clamp 30, which presses tip tray 16 against thru tip gasket 52 to form a seal between pipette tips 54 and thru tip gasket 52.

Actuator assembly 14 holds piston assembly 12 and tip tray 16. When actuator motor 28 turns ball screw 26, actuator motor 28 drives ball screw nut 24 to position actuator plate 20 along linear bearings 22. Actuator plate 20 is bolted to piston plate 34 to move pistons 32 through top seal plate 38, upper seal 40, wash plate upper seal retainer 42, wash chamber 44, wash plate 46, lower seal 48, cylinder block 50, and thru tip gasket 52. Retracting pistons 32 away from pipette tips 54 is an aspirate motion. During an aspirate motion, fluid or gas is aspirated into pipette tips 54. Advancing pistons 32 toward pipette tips 54 is a dispense motion. During a dispense motion, fluid or gas is dispensed from pipette tips 54.

Figure 3A:
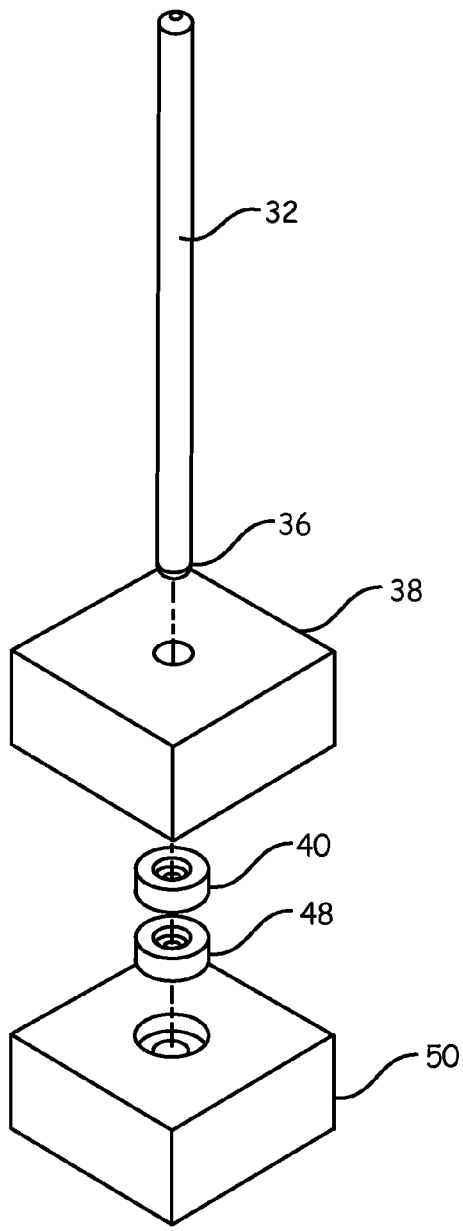
FIG. 3A is an exploded view of the sealing mechanism of the wash through pipettor of the present invention.
Figure 3B:
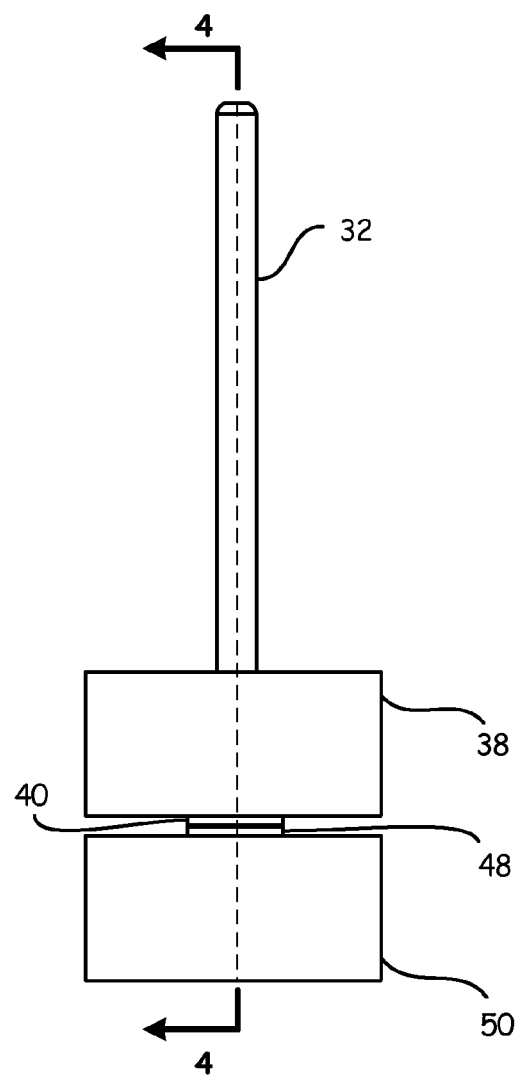
FIG. 3B is a side view of the sealing mechanism of the wash through pipettor of the present invention.
Figure 4A:
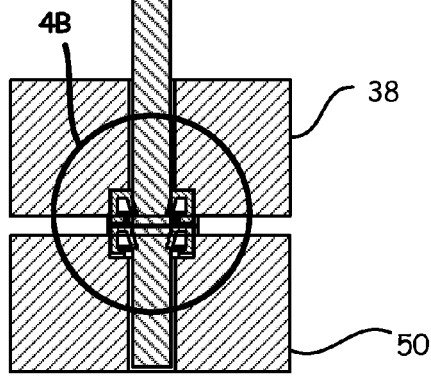
FIG. 4A is a cross-sectional view of the sealing mechanism of the wash through pipettor of the present invention along line 4-4 in FIG. 3B.
Figure 4B:
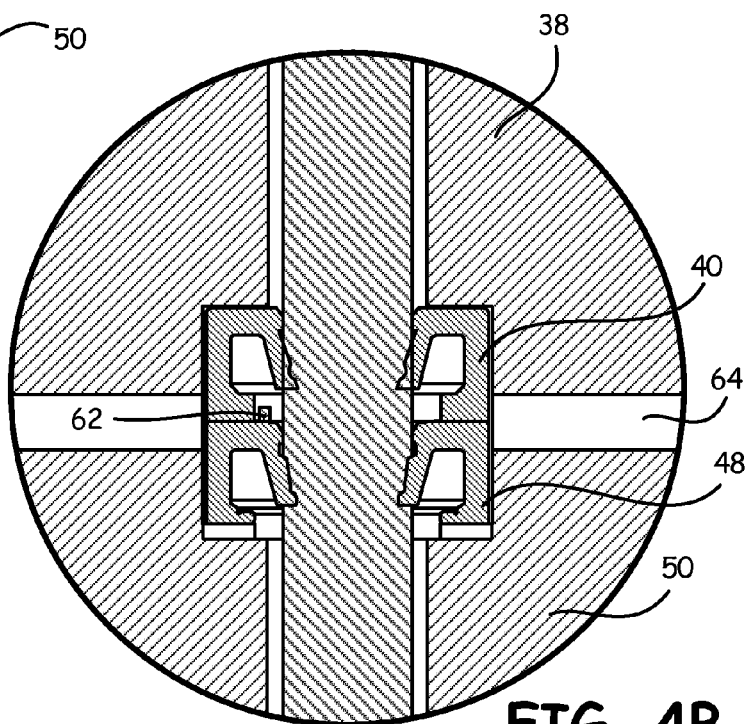
FIG. 4B is a zoomed-in view of the cross-sectional view of the sealing mechanism in FIG. 4A.

FIGS. 3A and 3B are an exploded view and a side view illustrating the sealing mechanism of wash through pipettor 10. FIG. 4A is a cross-sectional view of the sealing mechanism of wash through pipettor 10 along line 4-4 in FIG. 3B. FIG. 4B is a zoomed-in view of the cross-sectional view of the sealing mechanism in FIG. 4A. The sealing mechanism of wash through pipettor 10 includes pistons 32 with tapered tips 36, top seal plate 38, upper seal 40 with groove 62, lower seal 48, and cylinder block 50. Gap 64 provides a space between top seal plate 38 and cylinder block 50. Upper seal 40 is retained by lower seal 48 and lower seal 48 is retained by upper seal 40.

A wash cycle in wash through pipettor 10 begins by retracting pistons 32 until tapered tips 36 lose sealing contact with lower seal 48, acting as a mechanical valve by opening fluid flow channels 61 to wash chamber 44. Wash fluid, such as purified water, is supplied to supply port 56. Wash chamber 44 is pressurized, upper seal 40 becomes tighter and lower seal 48 becomes looser, and wash fluid floods wash chamber 44. Wash fluid flows through gap 64 into fluid flow channels 61. Groove 62 of upper seal 40 ensures that wash water can get between upper seal 40 and lower seal 48 into fluid flow channels 61. Tapered tips 36 of pistons 32 increase wash fluid flow into fluid channels 61 as pistons 32 are retracted partially to fully from lower seal 48.

Wash fluid flows through fluid flow channels 61, passing through wash plate 46, lower seal 48, cylinder block 50, and thru tip gasket 52, and washing out pipette tips 54. In an alternative embodiment, lower seal 48 may be a check valve with a cracking pressure suitable for opening with high pressure wash water, but remaining sealed for normal aspirate and dispense pressures, allowing wash fluid to flow into fluid channels 61 without retracting pistons 32. Wash through pipettor 10 may be positioned over a waste container to catch waste water as it flows out of pipette tips 54. The waste container may also be a bath type container where pipette tips 54 are submerged for cleaning the outside of pipette tips 54, with or without sonication.

After sufficiently washing the inside of each channel of fluid flow channels 61, supply port 56 is closed. Pistons 32 are advanced to pass through lower seal 48, closing off fluid flow channels 61 from wash chamber 44. Pistons 32 are further advanced to dispense excess wash fluid into the waste container. If the aspirate volume for the next operation is known, pistons 32 may be advanced a partial stroke sufficient for the needs of the next aspiration. This will save time and avoid drawing contaminants higher up in fluid flow channels 61. When the wash water dispense action is finished, the wash cycle is complete. At the end of a wash cycle, each channel of fluid flow channels 61 is filled with wash fluid 64 from upper seal 40 to the end of pipette tips 54.

Figure 5:
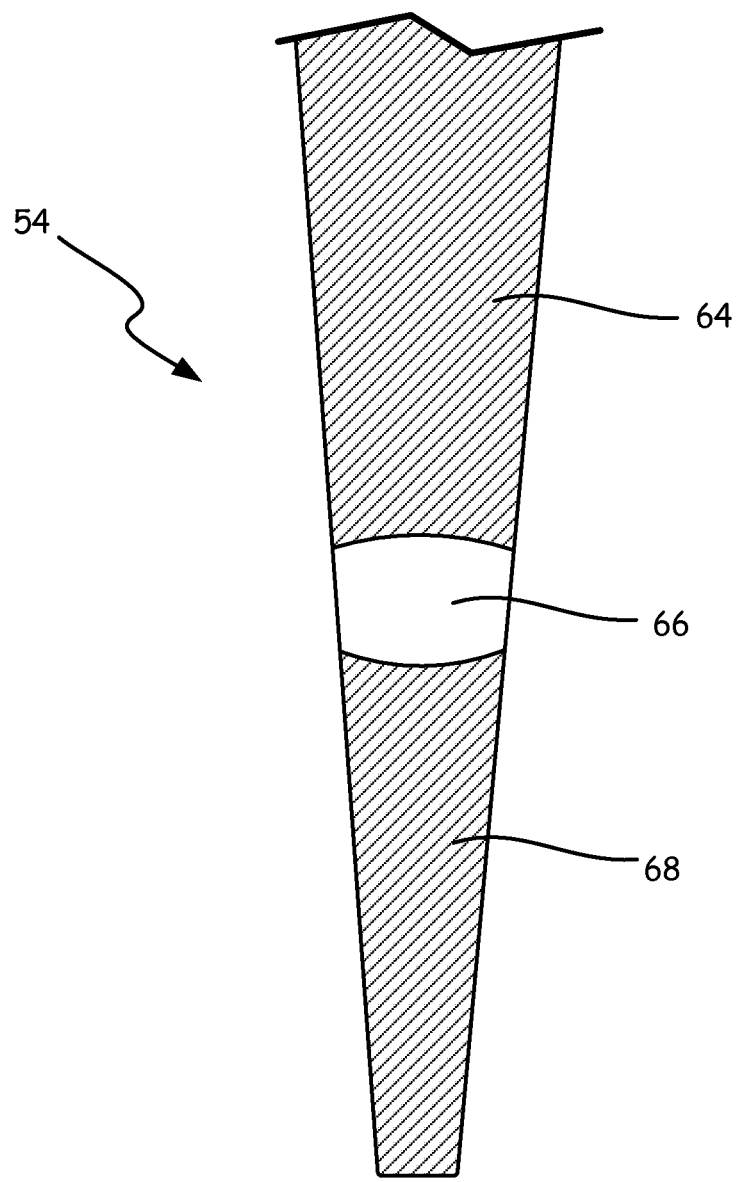
FIG. 5 is a cross-sectional view of a pipette tip of the wash through pipettor of the present invention.

FIG. 5 is a cross-sectional view of a pipette tip of pipette tips 54 of wash through pipettor 10, including wash fluid 64, air gap 66, and sample fluid 68. An aspirate cycle of wash through pipettor 10 begins after the conclusion of a wash cycle. Pistons 32 are retracted to aspirate air gap 66. Air gap 66 is required to separate wash fluid 64 from aspirated sample liquid 68. The size of air gap 66 will determine the rigidity of the coupling between the piston motion and the fluid motion. If air gap 66 is too small, the risk of wash fluid 64 and aspirated sample liquid 68 mixing is increased. If air gap 66 is too large, the coupling will become less rigid. When dispensing large volumes, air gap 66 can be made larger to guard against accidental dilution. When dispensing small volumes, air gap 66 is kept as small as possible. Since fluid flow channels 61 are mostly liquid filled, the issue of a varying vapor pressure is avoided. This is most significant when fluid flow channels 61 are filled with dry gas, and aspirating a liquid causes the gas to absorb vapor, creating a slow increase of vapor pressure. This issue is a common challenge with typical pipettors as the vapor pressure of the gas in each channel of fluid flow channels 61 varies when pipette tips are open to atmosphere as opposed to filled with sample liquids.

After air gap 66 is created, wash through pipettor 10 is positioned with pipette tips 54 dipped in a source plate. The source plate may be a plate with a plurality of wells, such as a microplate. Pistons 32 are retracted further to aspirate sample liquid 68 from the source plate. Pipette tips 54 are then retracted from the source plate. The velocity of retraction may be adjusted to influence the break-off behavior of the liquid at pipette tips 54 to increase aspiration accuracy.

After the aspiration cycle is complete, the dispense cycle begins by positioning pipette tips 54 over the target plate. There are many variations of dispensing methods that include pre-dispensing a small volume prior to making physical contact with the target. The cycle may include pre-moving the fluid up and down within pipette tips 54 to avoid a dry meniscus causing sample fluid 68 to not move freely within fluid flow channels 61. Sample fluid 68 is dispensed by advancing pistons 32 through fluid flow channels 61 toward and/or into pipette tips 54. After the dispense cycle is complete and sample fluid 68 makes contact with the target, pipette tips 54 are retracted away from the target plate. The velocity of retraction may be adjusted to influence the break-off behavior of the liquid at pipette tips 54 to increase dispensing accuracy. The dispense cycle is often repeated several times for a single aspirate cycle. After the dispensing cycles are complete, the wash cycle is performed.

In alternative embodiments, compressed air may be supplied through supply port 56 to push out wash liquid 64, or to perform drying of fluid flow channels 61. Wash cycles may include alternating wash liquid with air to operate wash through pipettor 10 with the advantages of the wash through cleaning, but avoid using wash liquid 64 with air gap 66. When aspirating and dispensing in the air only mode, pistons 32 are capable of advancing far into pipette tips 54, minimizing the volume of air in fluid flow channels 61, causing the coupling between the piston motion and the fluid motion to be more rigid and improving dispense volume accuracy.

Although the present invention has been described with reference to preferred embodiments, workers skilled in the art will recognize that changes may be made in form and detail without departing from the spirit and scope of the invention.

The invention claimed is:

1. A pipettor comprising:
   an upper plate;

a lower plate;

a wash chamber defined by a space between the upper plate and the lower plate;

an upper seal with a groove and a lower seal, the upper seal located below the upper plate and retained by the lower seal, and the lower seal located above the lower plate and retained by the upper seal;

a gasket located below the lower plate;

a pipette tip retained by the gasket;

a piston with a tapered tip that passes through the upper plate, the upper seal, the lower seal, the lower plate, and the gasket into the pipette tip; wherein the upper seal and the lower seal isolate the piston from the wash chamber;

a channel defined by the piston and extending into the pipette tip; and an actuator for advancing and retracting the piston;

wherein, when the actuator retracts the piston such that the piston loses sealing contact with the lower seal and the wash chamber is supplied with a wash fluid and pressurized, the wash fluid passes through the groove in the upper seal and into the channel defined by the piston.

2. The pipettor of claim 1, wherein the lower seal is a check valve.

3. The pipettor of claim 1, wherein the pipettor comprises a plurality of pipette tips, pistons, and channels; each pipette tip retained by the gasket, each piston passing through the upper plate, the upper seal, the lower seal, the lower plate, and the gasket into one of the pipette tips; and each channel defined by one of the pistons.

4. A method of operating a pipettor, the method comprising:

retracting a piston with a tapered tip such that the piston passes through a lower plate and a lower seal and loses sealing contact with the lower seal, the lower seal retaining an upper seal with a groove and the upper seal retaining the lower seal;

supplying a wash chamber surrounding the lower seal and the upper seal with wash fluid;

pressurizing the wash chamber such that the wash fluid passes through the groove of the upper seal into a channel defined by the piston, the channel passing through a lower plate below the lower seal, through a gasket below the lower plate, and into a pipette tip retained by the gasket; and advancing the piston such that the wash fluid flows through the channel, filling the pipette tip and such that the piston seals off the channel from the wash chamber.

5. The method of claim 4, and further comprising:

retracting the piston to aspirate an air gap in the pipette tip below the wash fluid;

dipping the pipette tip into a sample; and further retracting the piston to aspirate the sample.

6. The method of claim 5, and further comprising advancing the piston to dispense the sample.

7. The method of claim 4, wherein the pipettor comprises a plurality of pistons, channels, and pipette tips.

* * * * *